(12) United States Patent
Wurtz

(10) Patent No.: US 7,317,802 B2
(45) Date of Patent: Jan. 8, 2008

(54) ACTIVE-NOISE-REDUCTION HEADSETS WITH FRONT-CAVITY VENTING

(75) Inventor: Michael Jon Wurtz, St. Paul, MN (US)

(73) Assignee: LightSPEED Aviation, Inc., Portland, OR (US)

( * ) Notice: Subject to any disclaimer, the term of this patent is extended or adjusted under 35 U.S.C. 154(b) by 0 days.

(21) Appl. No.: 10/201,540

(22) Filed: Jul. 22, 2002

(65) Prior Publication Data

US 2003/0095670 A1 May 22, 2003

(51) Int. Cl.
*A61F 11/06* (2006.01)
*G10K 11/16* (2006.01)
*H03B 29/00* (2006.01)

(52) U.S. Cl. .......................... 381/71.6; 381/72; 381/74

(58) Field of Classification Search ................ 381/74, 381/71.6, 317, 322, 324, 370, 371, 72
See application file for complete search history.

(56) References Cited

U.S. PATENT DOCUMENTS

| | | | | |
|---|---|---|---|---|
| 3,637,040 A | * | 1/1972 | Gorman | 181/175 |
| 4,005,278 A | * | 1/1977 | Gorike | 381/373 |
| 4,160,135 A | | 7/1979 | Gorike | 179/182 R |
| 4,239,945 A | * | 12/1980 | Atoji et al. | 381/371 |
| 4,455,675 A | * | 6/1984 | Bose et al. | 381/74 |
| 4,922,542 A | * | 5/1990 | Sapiejewski | 381/373 |
| 5,020,163 A | * | 6/1991 | Aileo et al. | 2/209 |
| 5,182,774 A | | 1/1993 | Bourk | 381/71 |
| 5,590,208 A | | 12/1996 | Koyano et al. | |
| 5,604,813 A | | 2/1997 | Evans et al. | 381/71 |
| 5,729,605 A | | 3/1998 | Bobisuthi et al. | |
| 5,748,749 A | | 5/1998 | Miller et al. | |
| 5,987,144 A | | 11/1999 | Carme et al. | |
| 6,041,126 A | * | 3/2000 | Terai et al. | 381/71.6 |
| 2002/0015501 A1 | | 2/2002 | Sapiejewski | |

FOREIGN PATENT DOCUMENTS

EP 0232096 * 8/1987

OTHER PUBLICATIONS

"ANR 101 Section 1: The Basics of ANR", *LightSPEED Aviation, Inc.*, http://www.lightspeed.com,(2000),pp. 1-6.
"ANR 101, A Tutorial on Active Noise Reduction", *LightSPEED Aviation, Inc.*, http://www.lightspeed.com,(2000),pp. 1-2.
Busch, M. , "AVweb Product Report: LightSPEED Technologies 25XL Active Noise Reduction Headset", file://C:\TMP\LightSPEED 25XL ANR Headset.htm,(1997),pp. 1-7.

* cited by examiner

*Primary Examiner*—Xu Mei
(74) *Attorney, Agent, or Firm*—Schwegman, Lundberg & Woessner, P.A.; Eduardo E. Drake

(57) ABSTRACT

Active-noise-reduction (ANR) headsets protect the hearing of their users from loud persistent noises, such as airplane engines and construction equipment. These headsets generally include ear speakers and special circuitry to cancel or suppress certain types of loud persistent noises. One problem the present inventor recognized with active headsets, particularly those manufactured in mass quantities, concerns the performance variations that stem from inevitable variations in the fit of their earcups against heads of their users. For example, in putting on and taking off these headsets, some users experience low-pitched noises. Accordingly, the inventor devised, among other things, headsets that include front-cavity vents for equalizing the pressure between a front cavity portion of an earcup and an ambient environment.

11 Claims, 16 Drawing Sheets

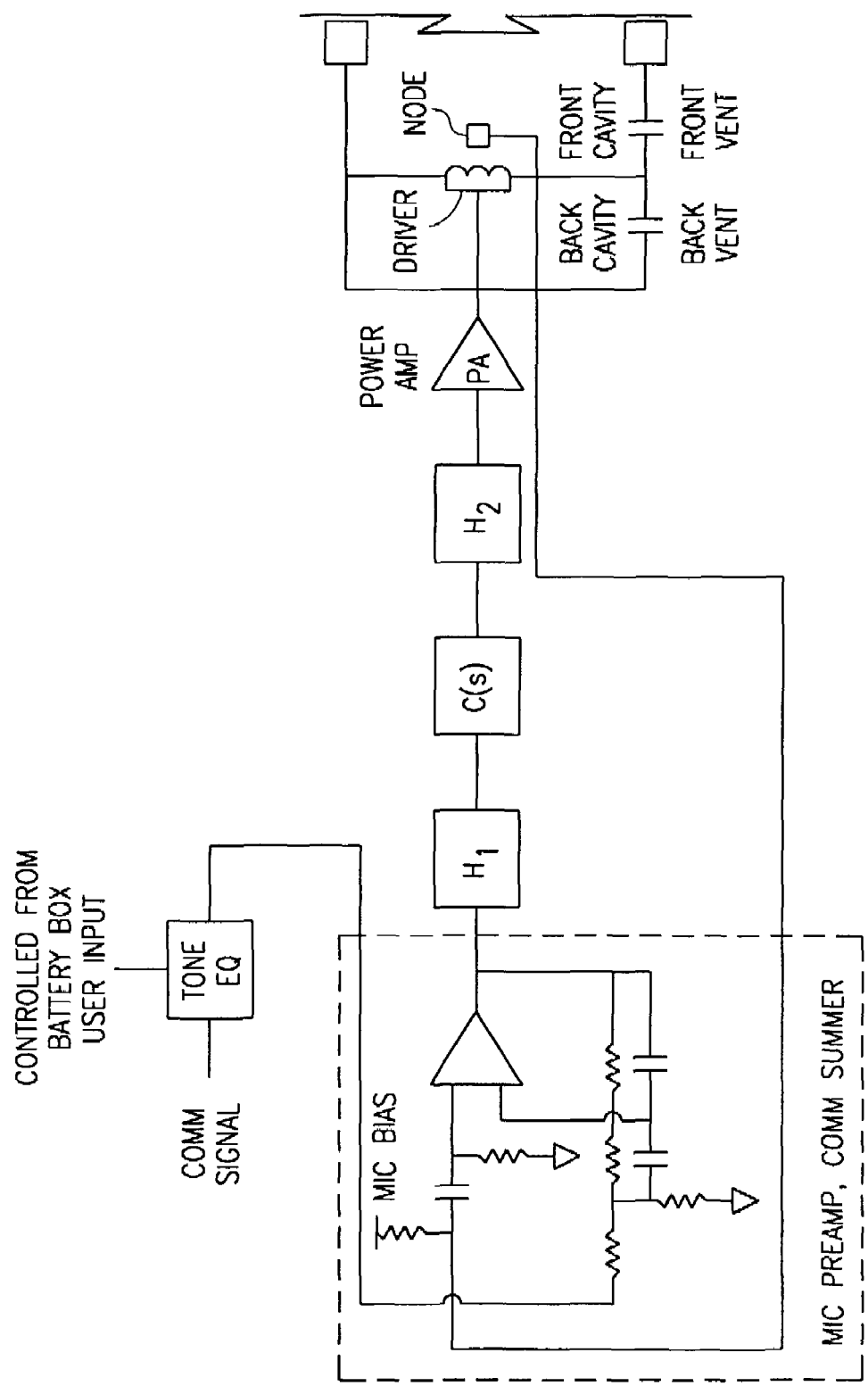
FIG. A1

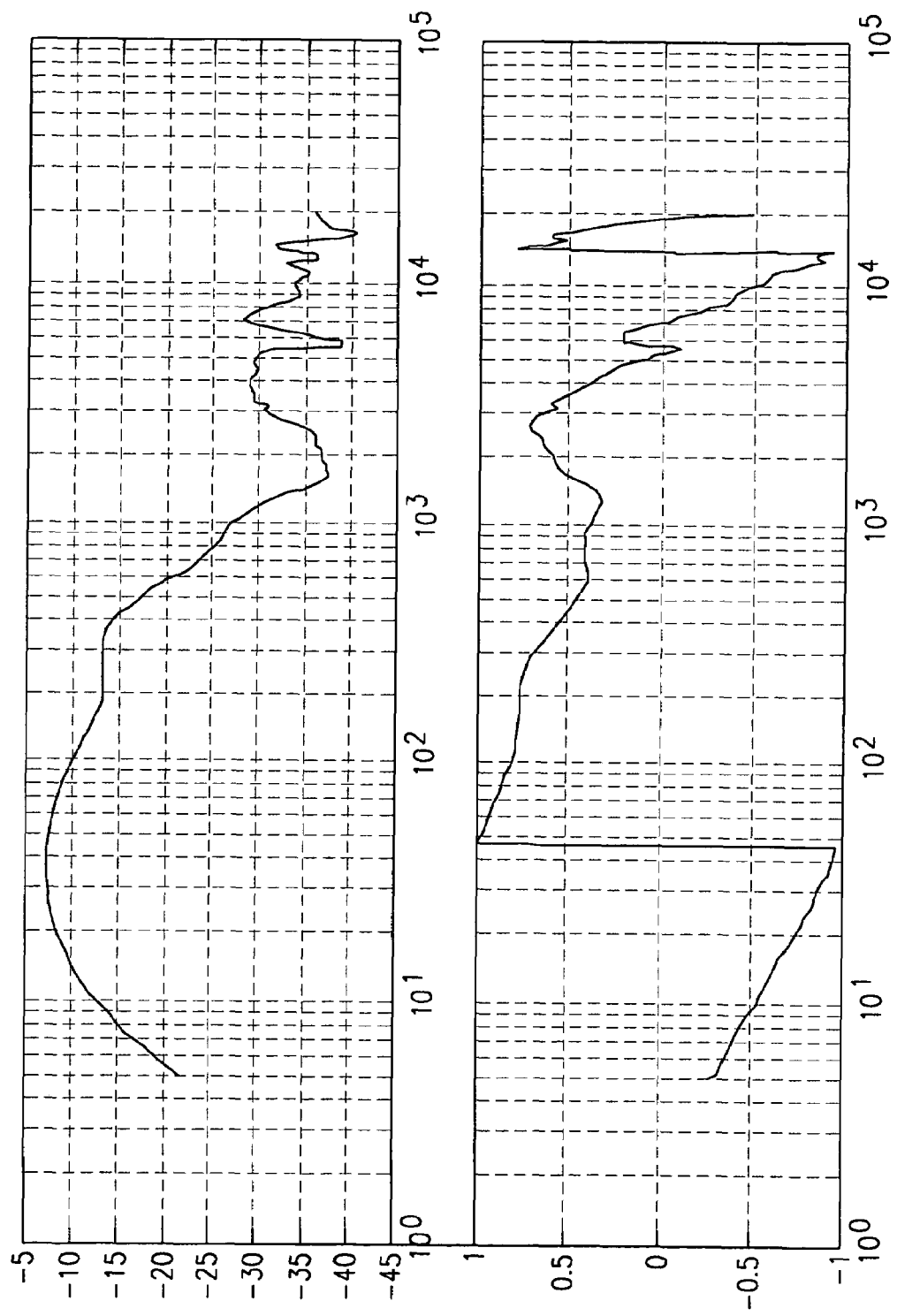
FIG. A2

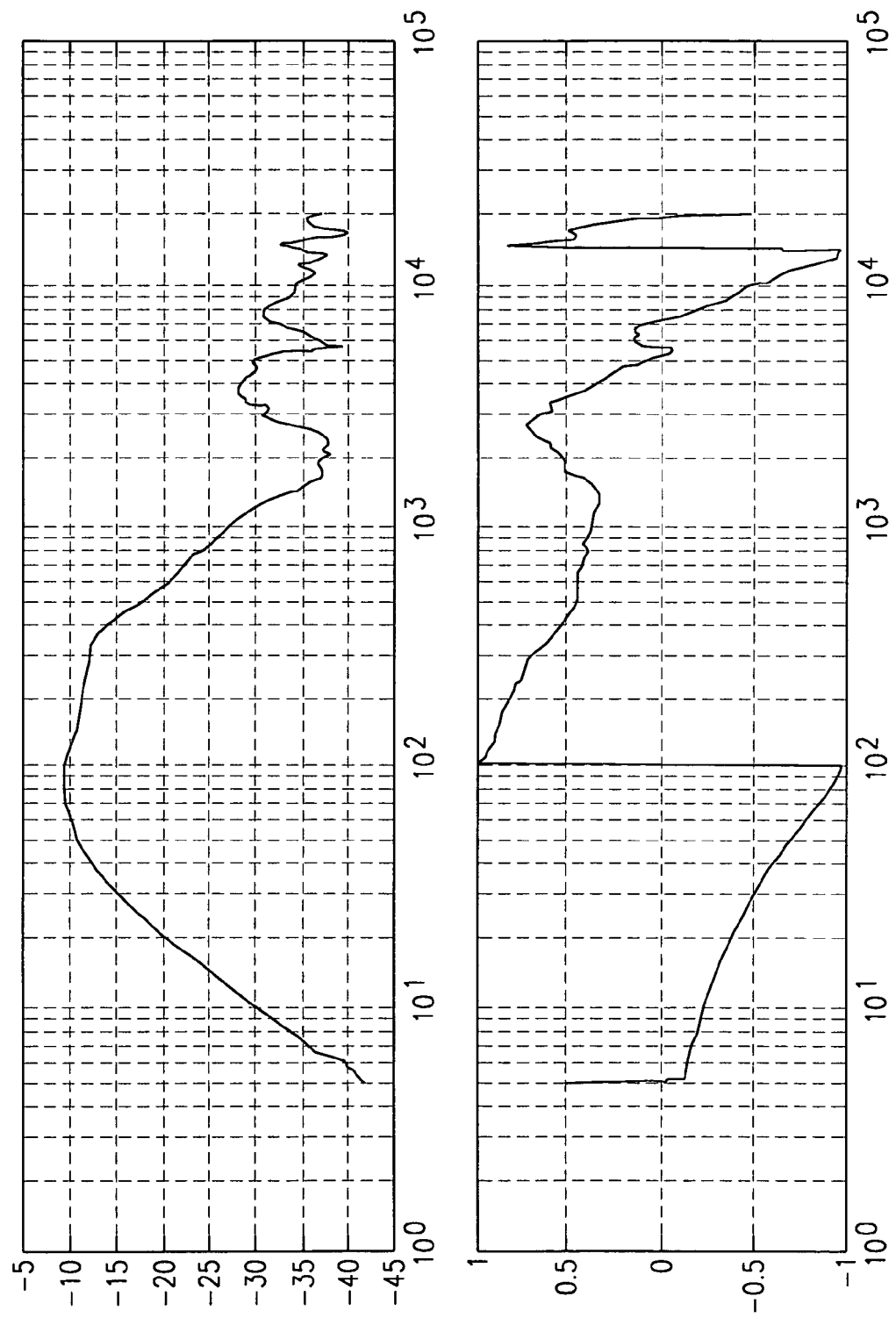
FIG. A3

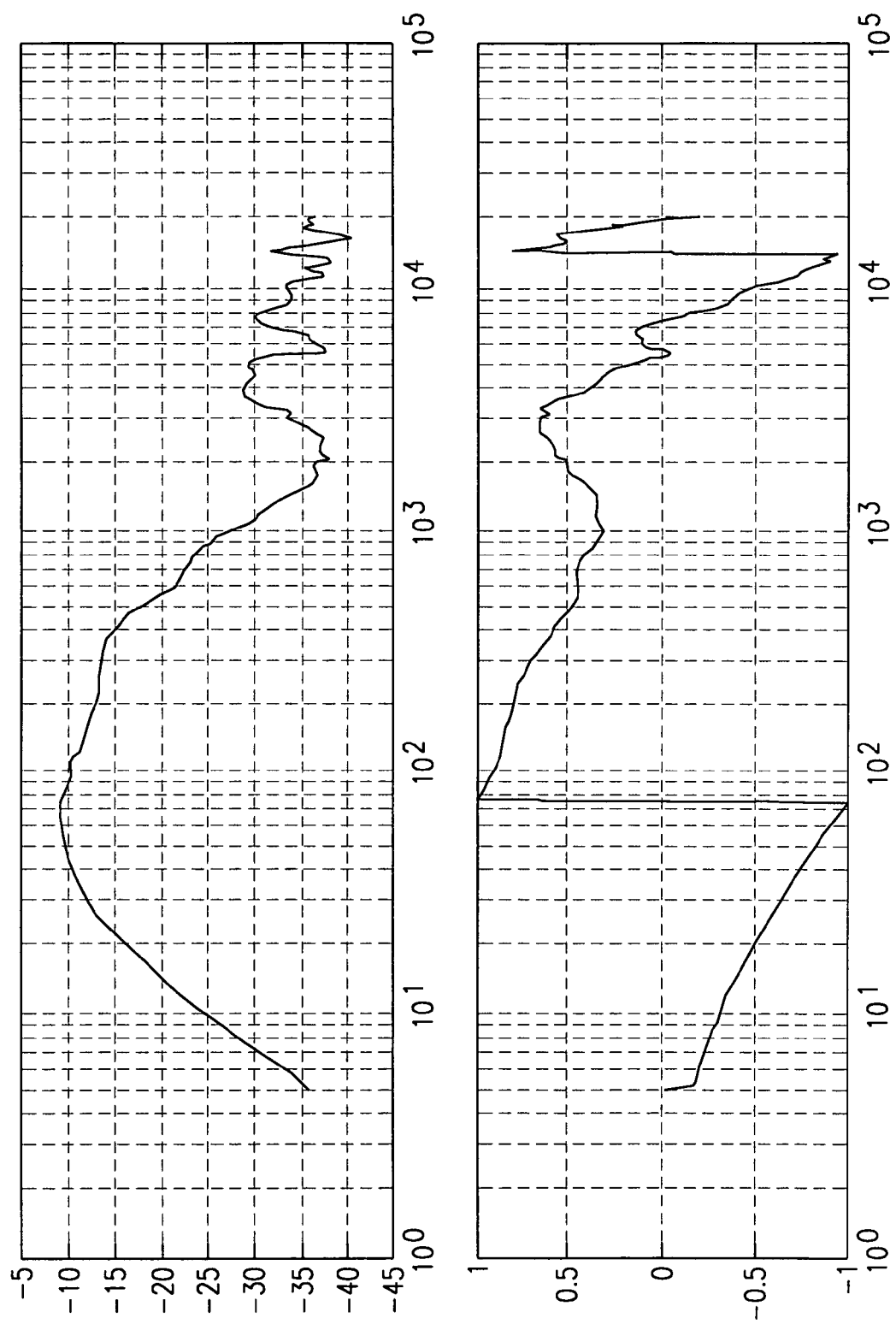
FIG. A4

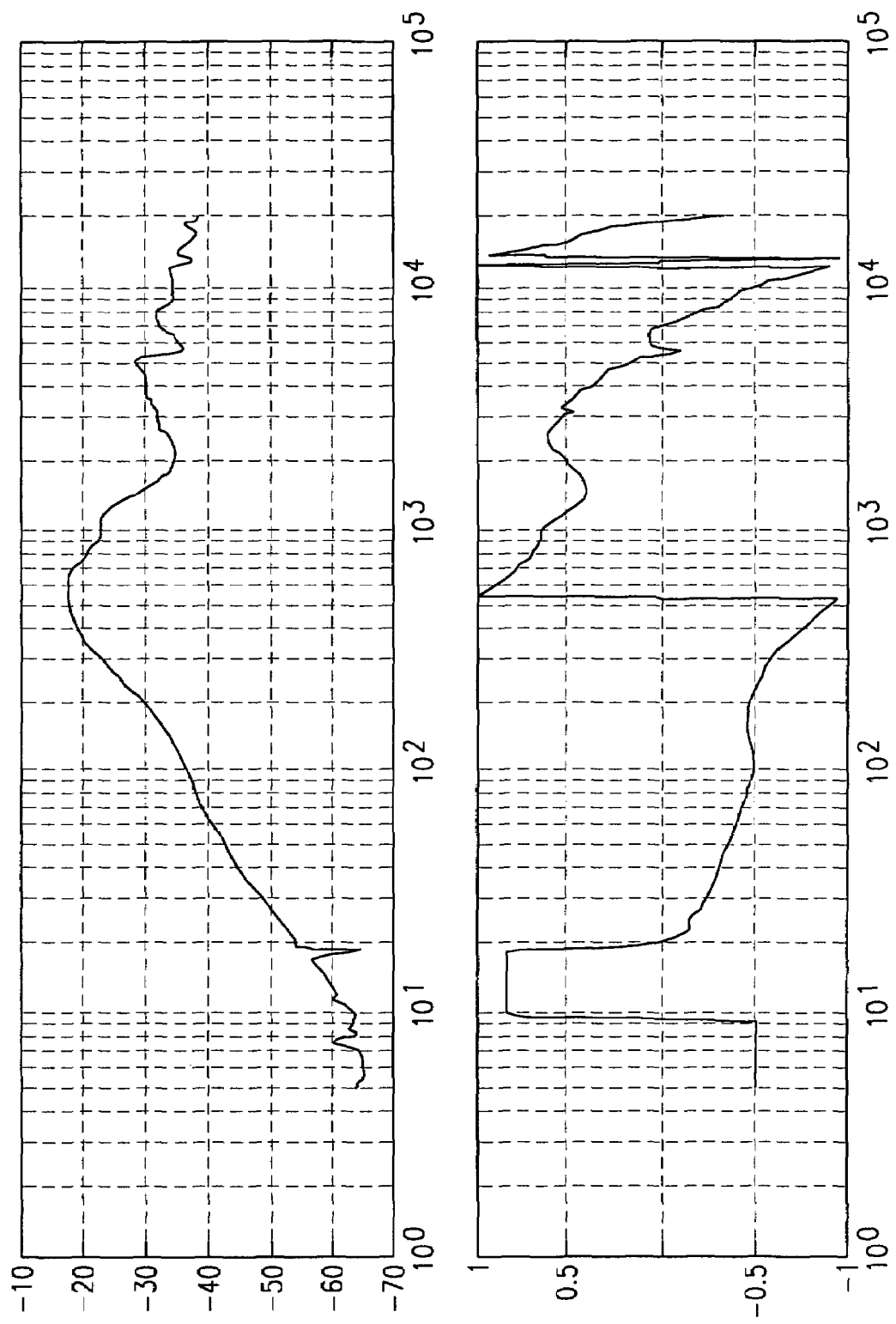
FIG. A5

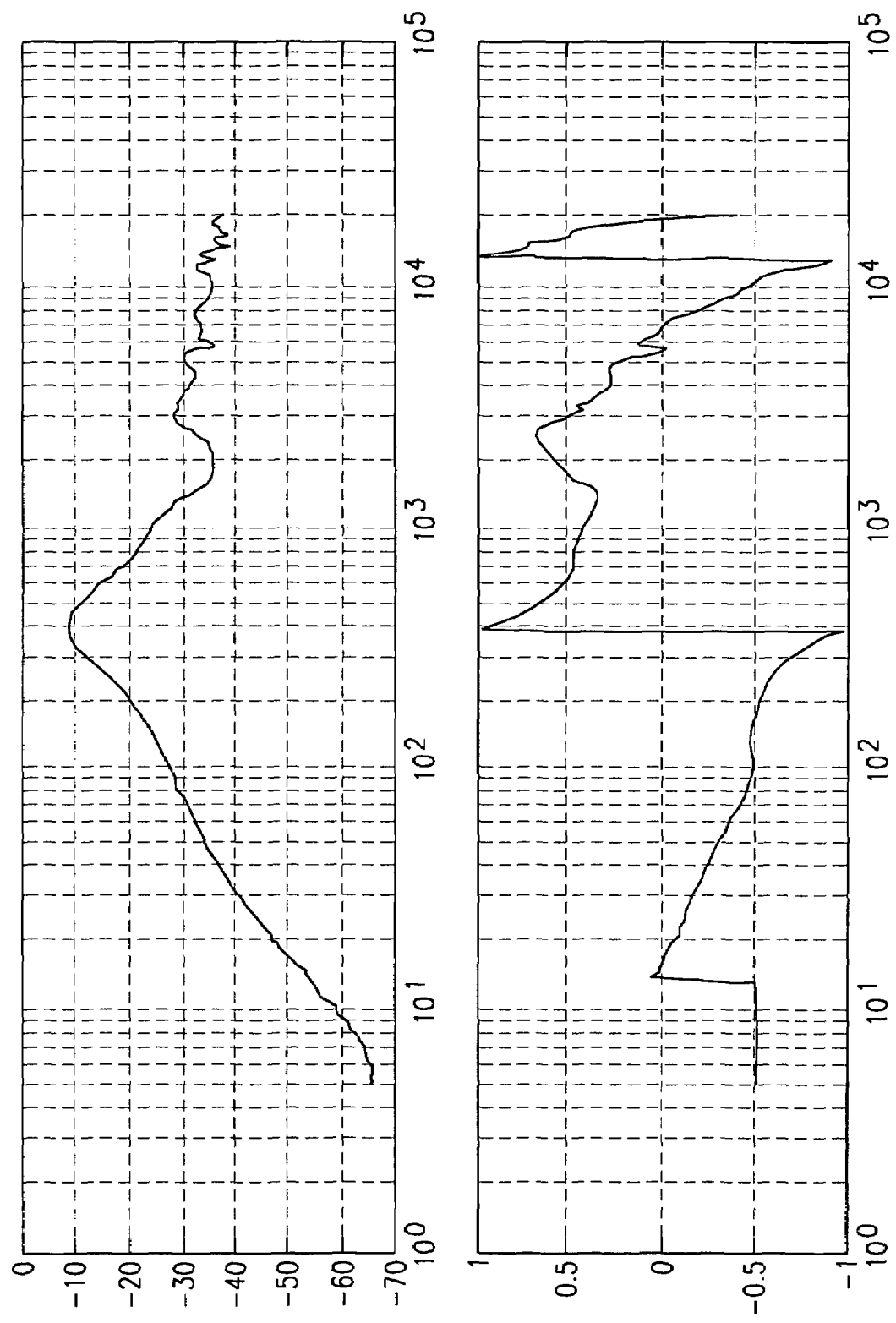
FIG. A6

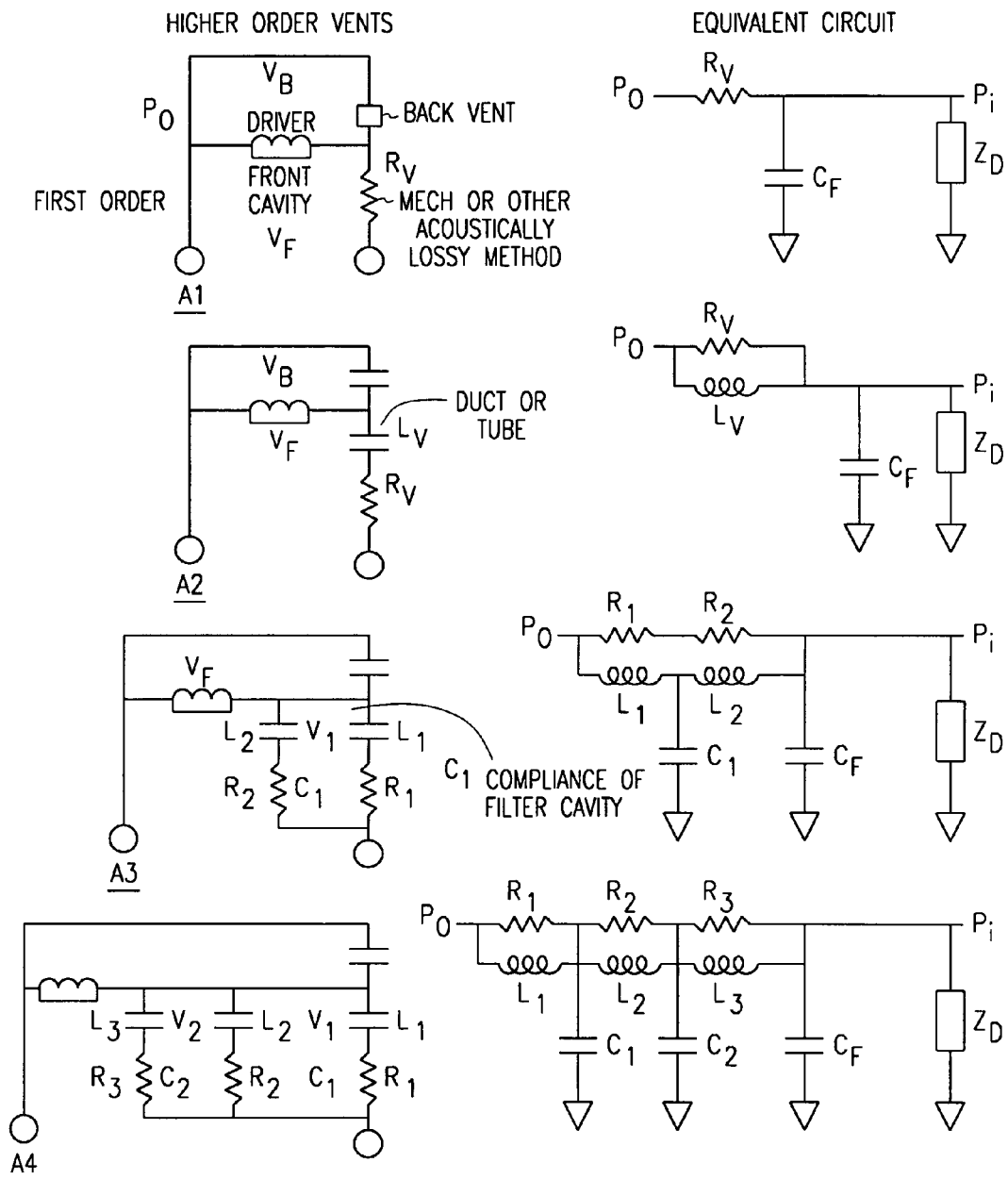
FIG. B

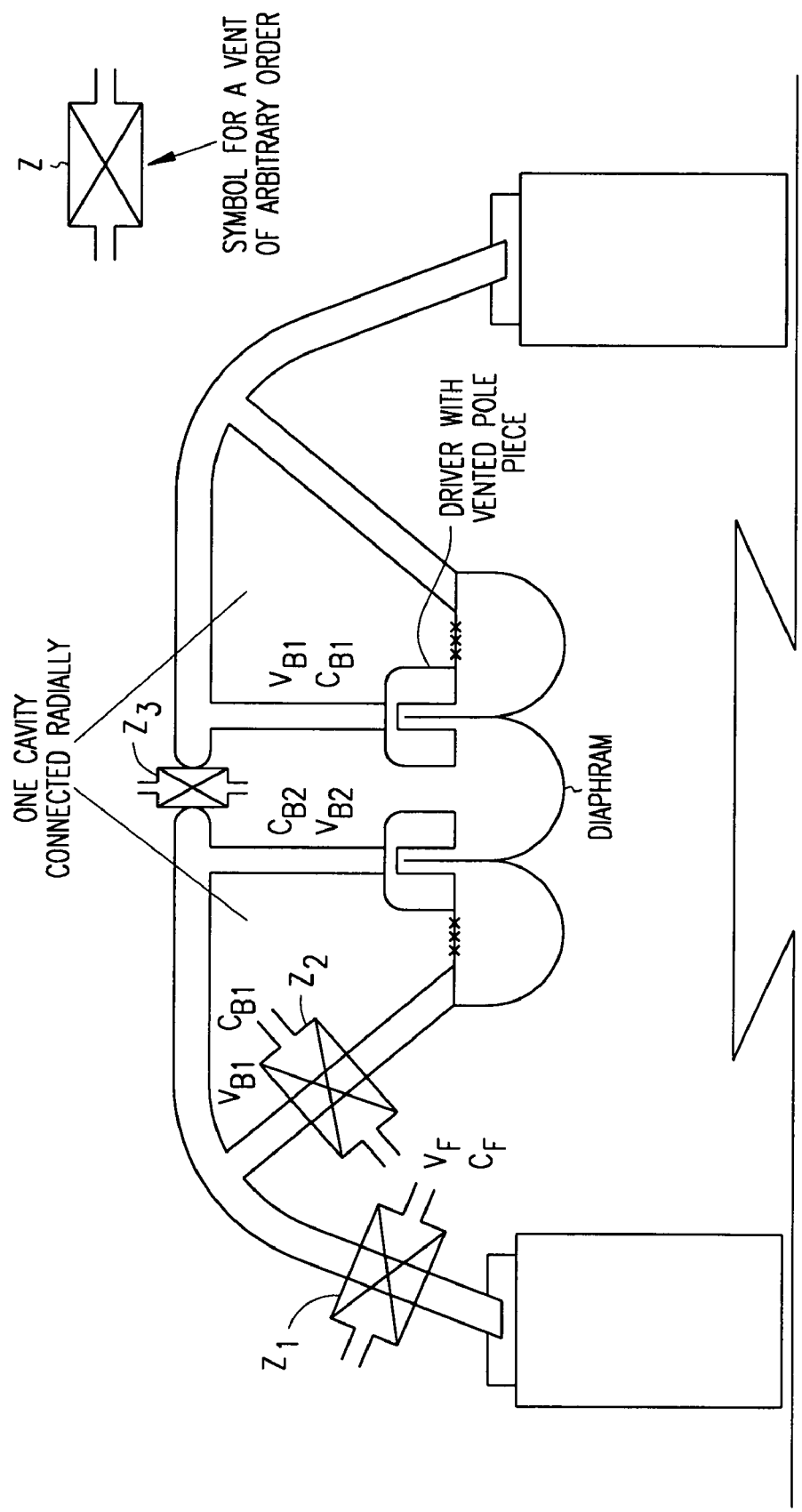
FIG. C

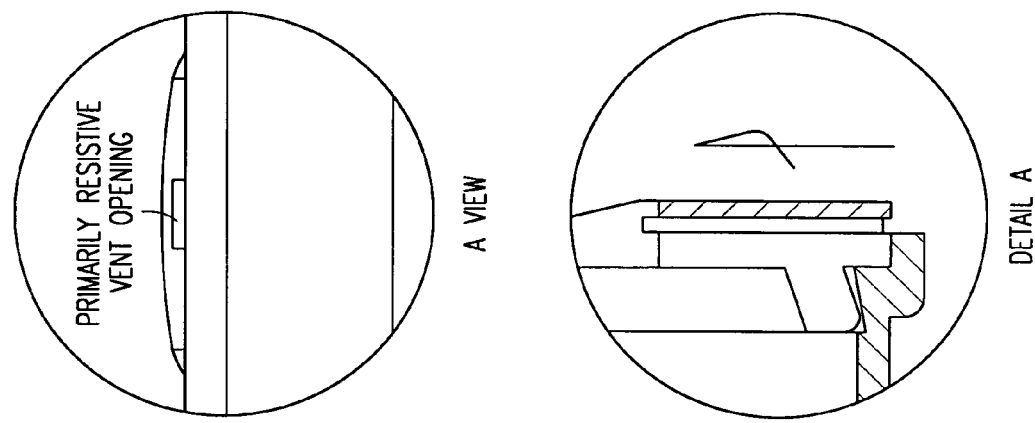
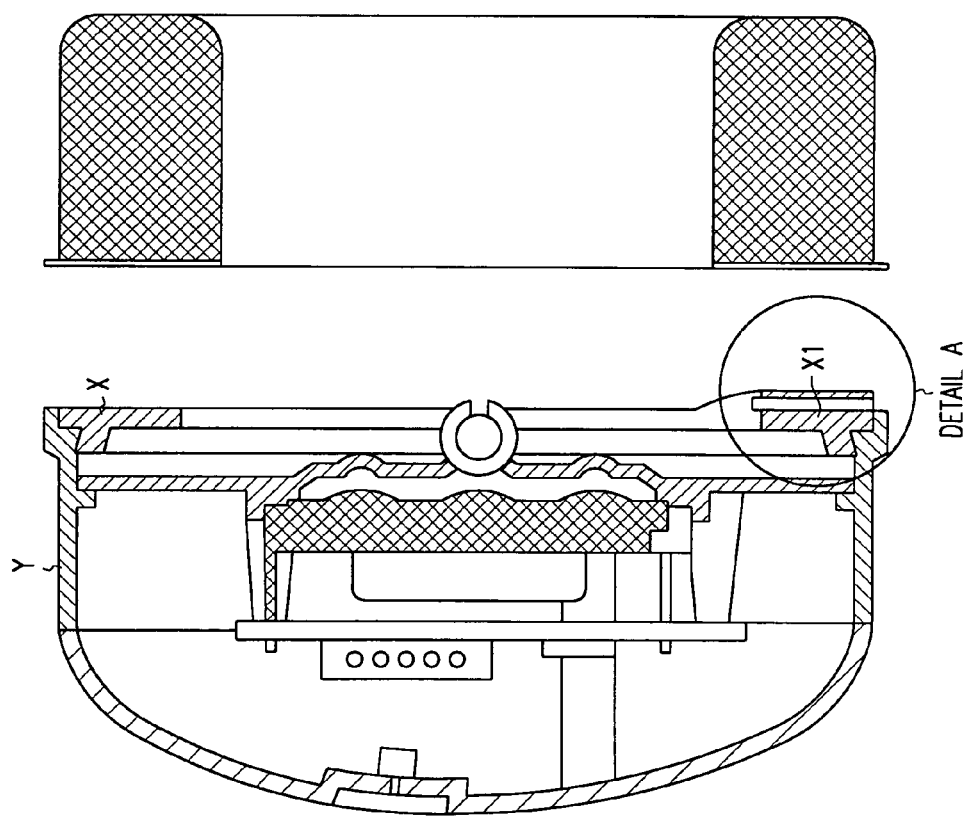
FIG. D1

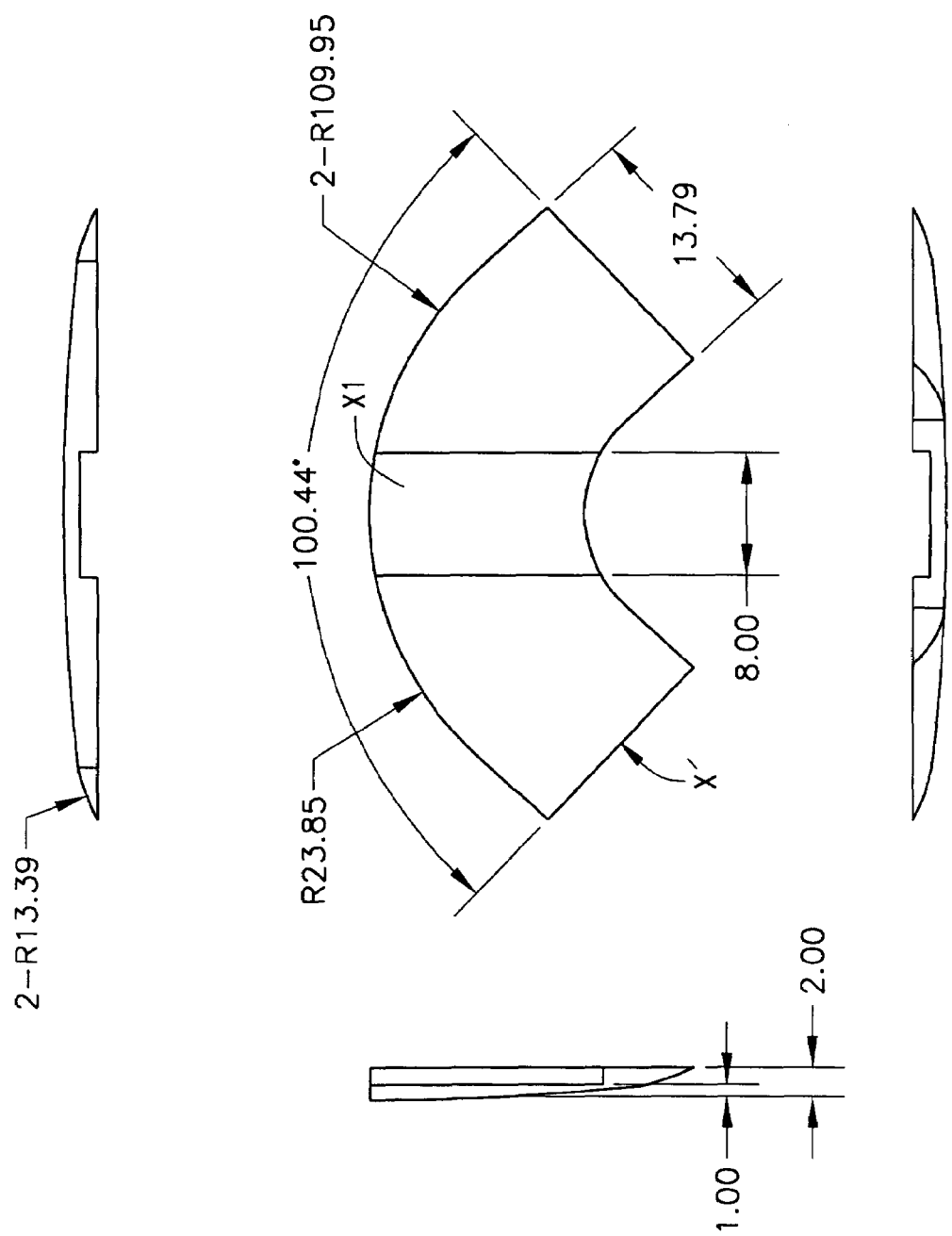
FIG. D2

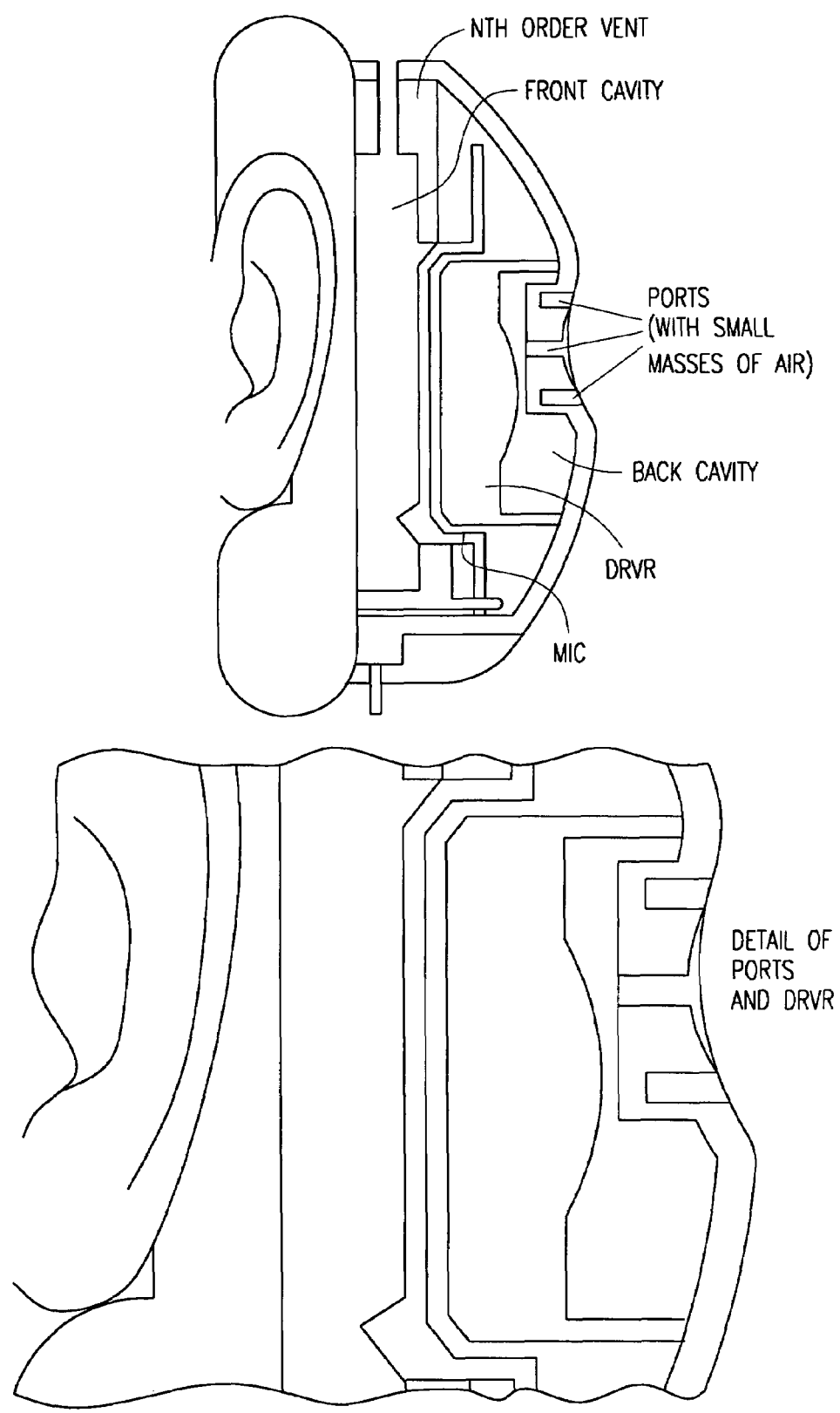
FIG. E

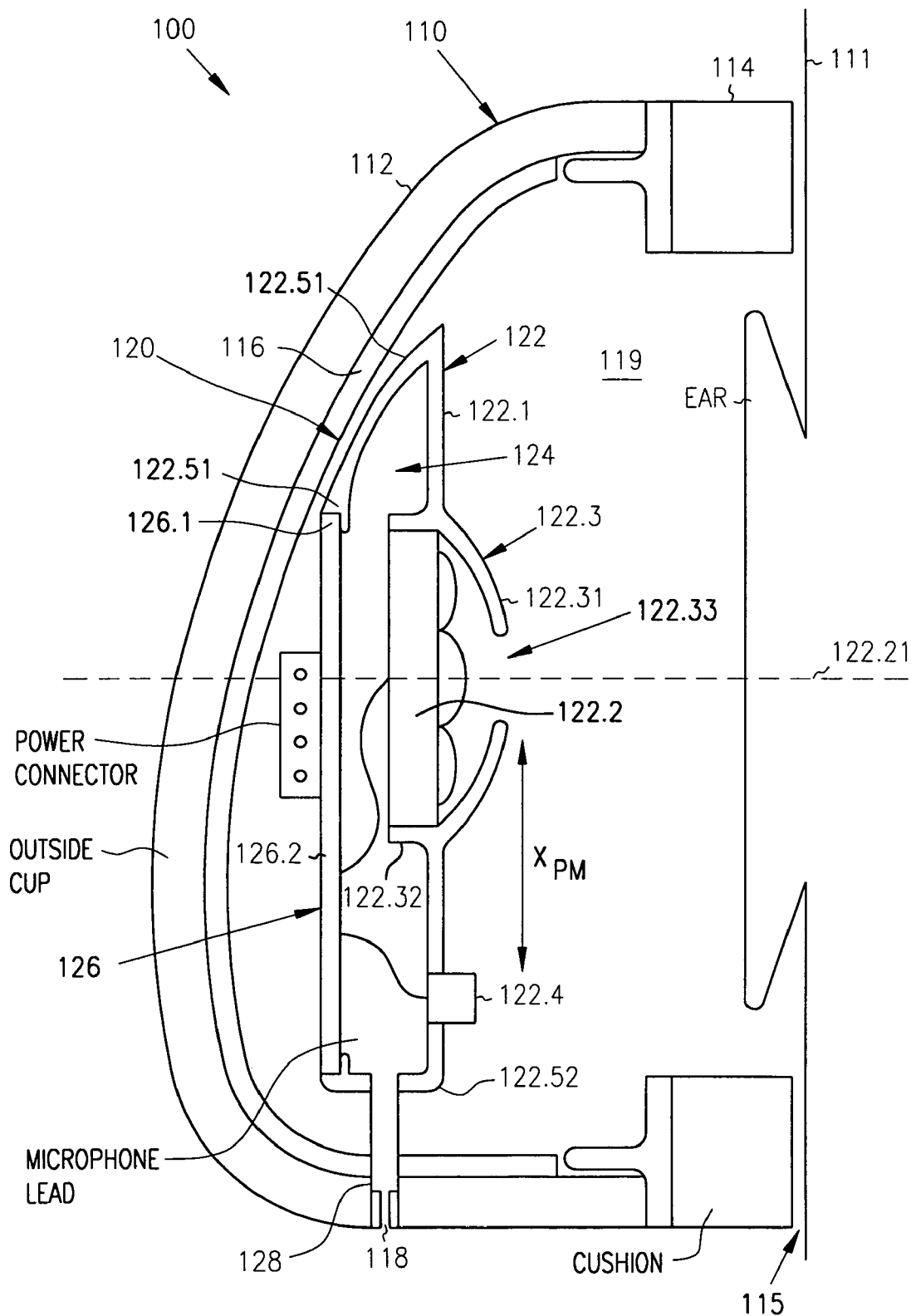
FIG. F1

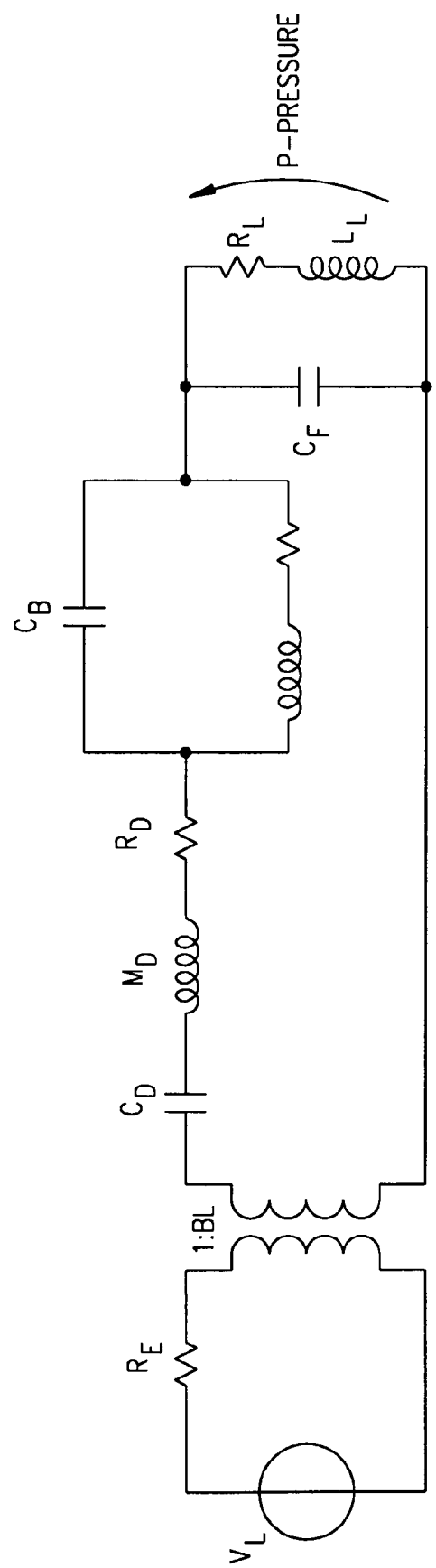
FIG. F2

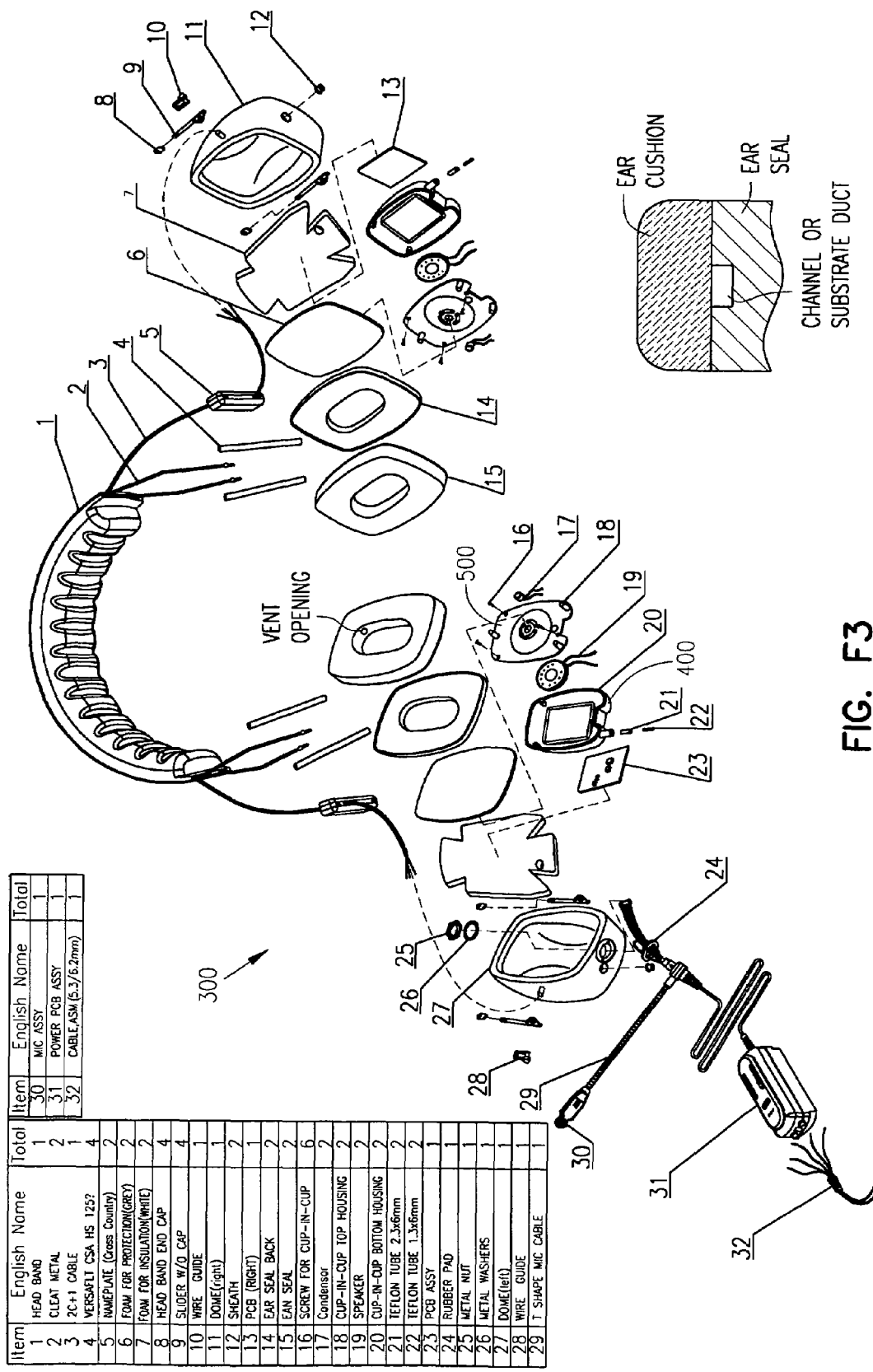

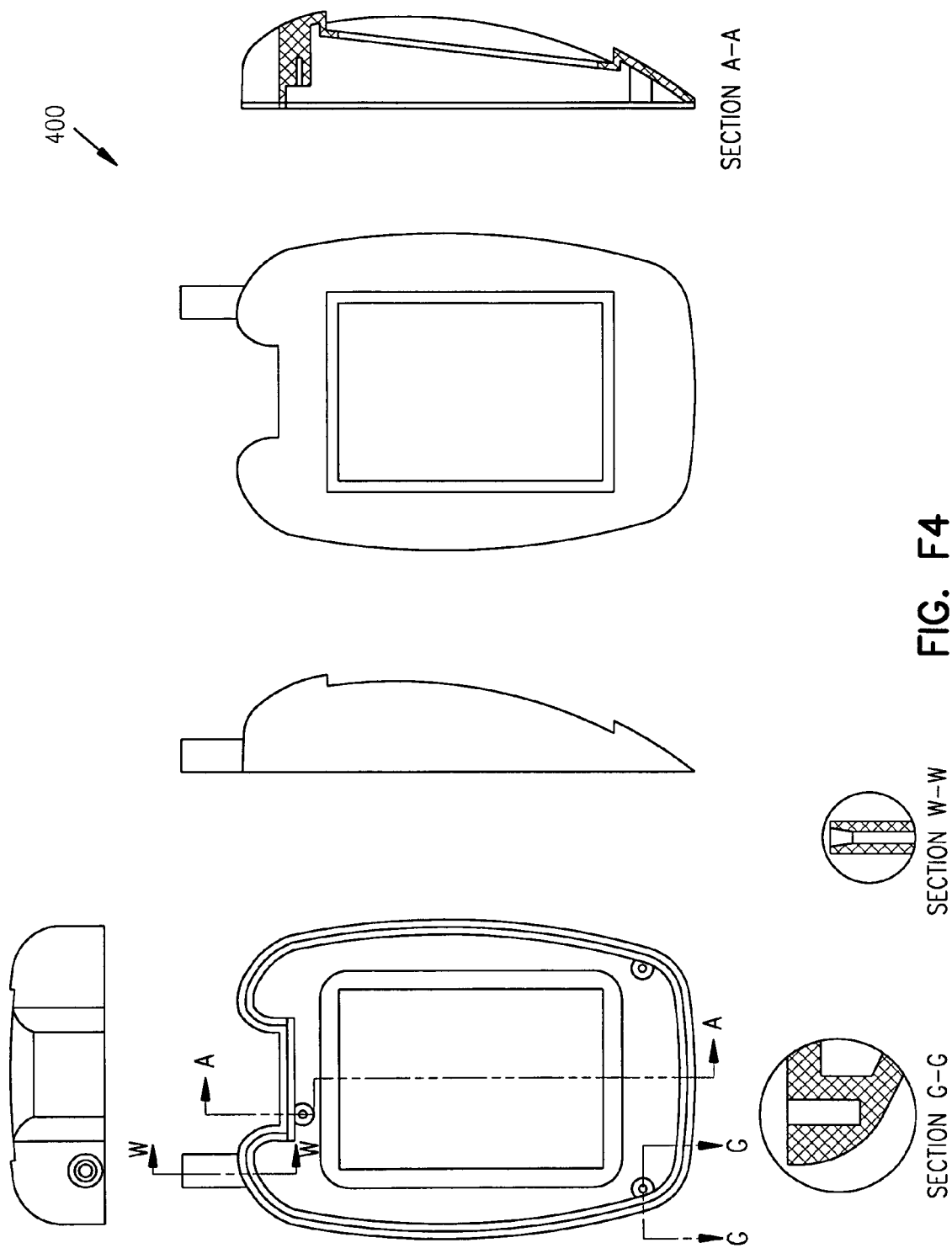
FIG. F4

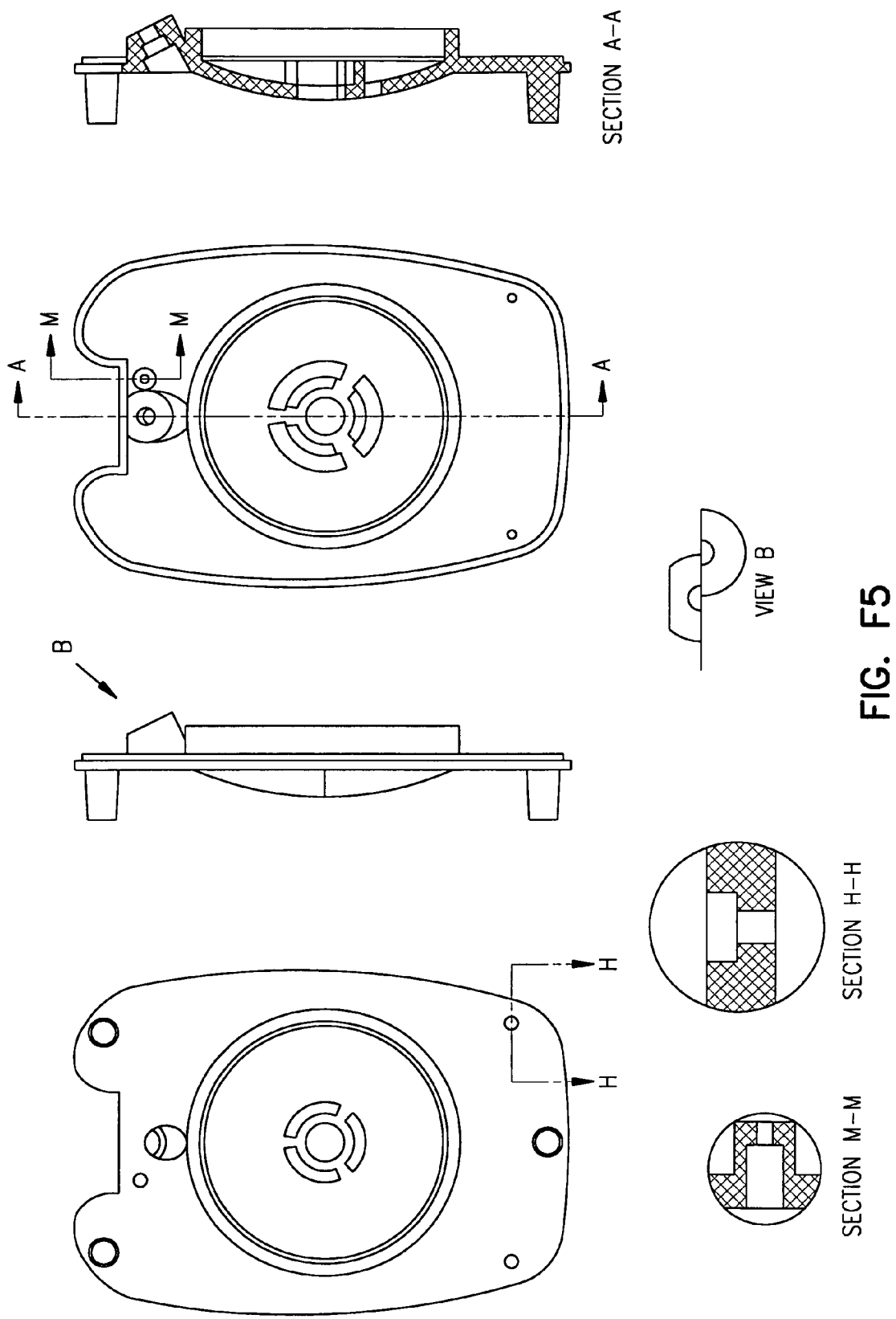
FIG. F5

ACTIVE-NOISE-REDUCTION HEADSETS WITH FRONT-CAVITY VENTING

CROSS-REFERENCE TO RELATED APPLICATIONS

This patent application claims priority to U.S. patent application Ser. No. 09/916,191 filed Jul. 25, 2001 now U.S. Pat. No. 6,735,316, which itself claims priority to U.S. provisional patent application 60/220,781 filed Jul. 25, 2000. Both applications are incorporated herein by reference, and it is to be understood that each embodiment in these applications includes one or more front-cavity vents, in accord with one or more other portions of this document.

TECHNICAL FIELD

The present invention concerns automatic noise-reduction systems and headsets, especially methods and techniques for promoting their stability.

BACKGROUND

Automatic noise-reduction (ANR) headsets typically include two earcups which are worn over ears of users to enhance or protect their hearing in environments, such as airplanes and construction sites, that have loud persistent noises. These headsets include ear speakers and ANR circuitry. The ANR circuitry senses sound in certain frequency ranges and attempts to cancel or suppress it by forcing the ear speakers to vibrate in opposition to it.

One problem that the present inventor recognized with some ANR headsets is that their performance can vary from person to person based on how well the earcups fit the head of a user. For example, some systems become unstable and oscillate during removal from the head of user and/or when subject to a tight fit against a user's head. The oscillations can be perceived by a user as high- or low-pitched noises, which can not only annoy the user, but also can suggest that the headsets are defective or poorly made.

Accordingly, the inventor has recognized a need for headsets that are more tolerant of user-fit variations.

SUMMARY

To address this and/or other needs, the inventor devised, among other things, exemplary ANR earcup structures which include one or more air passages or vents between the front cavity of the earcup (that is, the cavity between an ear speaker and the head of a user) and the exterior of the earcup. The inclusion of the one or more vents limits the effect of inevitable fit variations on the frequency response of the ANR circuitry, thereby promoting stable operation.

BRIEF DESCRIPTION OF DRAWINGS

FIG. A1 is a block diagram of an exemplary implementation of a closed-loop ANR system which corresponds to one or more embodiments of the present invention. FIGS. A2-A6 are exemplary frequency responses for an ANR system.

FIG. B includes several simplified schematics of equivalent electric circuits corresponding to one or more embodiments of the present invention FIG. C is a cross-sectional view of an earcup having an ANR driver with a vented pole piece.

FIG. D1 is a cross-sectional view of an ANR earcup assembly which includes a vent X1 and corresponds to one or more embodiments of the present invention.

FIG. D2 shows another view of vent X1, particularly its location on a rounded corner portion of ear-seal backing X.

FIG. E shows various cross-sectional views of an exemplary ANR headset corresponding to one or more embodiments of the invention.

FIG. F1 is a cross-section of one half of an ANR headset, which corresponds to one or more embodiments of the invention FIG. F2 is a simplified schematic of an equivalent electric circuit 200 corresponding to one or more embodiments of the present invention.

FIG. F3 is an exploded view of an exemplary active-noise-reduction headset 300 incorporating teachings of the present invention. One or more front-cavity vents, in accord with one or more other portions of this disclosure are also included.

FIG. F4 includes front, side, and back views of a bottom housing shown in FIG. F3.

FIG. F5 includes front, side, and back views of a top housing shown in FIG. F3.

DESCRIPTION OF SOME EXEMPLARY EMBODIMENTS

The following detailed description, which references and incorporates the attached Figures, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Active Noise Reduction (ANR) Using Closed-Loop Control Techniques

FIG. A1 shows an exemplary advanced implementation of a closed-loop ANR system. One or more elements can be omitted and closed loop ANR can still be obtained.

The microphone senses the internal acoustic pressure, which is amplified by the preamp/summer. The signal from the preamp/summer is processed by the filters H1, H2, and an optional frequency dependent compressor that extends the usefulness of the ANR systems to higher sound pressure environments. The power amplifier drives the speaker element. This ANR system creates a closed loop control system that reduces the internal pressure at the sense microphone in the front cavity by the relationship:

$$A = Ni/No = Ap*(1/1 - H1*H2*C*Tdm),$$

where
- A is the total attenuation at the microphone;
- Ni in the Noise pressure at the microphone;
- No is the outside noise pressure;
- H1,H1 are filters optimized to minimize A over the desired range while meeting the Nyquist stability criteria;
- C is a frequency dependent compressor that changes its characteristics in a frequency dependent manner decreasing the gain at low frequencies to prevent clipping of the PA or other stages. C is controlled by one or more output voltages in the system, typically at the output of the PA. The benefit of controlling from multiple points is that interstage clipping can be prevented without requiring the PA to have excessive gain. Tdm=Vi/Vo, where Vi is the electrical input to the driver, and Vo is the electrical output of the microphone.

In conventional ANR systems that are designed to be used by the general population, a significant design problem is the response changes to Tdm with various users. For example, a large headed, balding user, who doesn't use glasses, might have a Tdm response as in FIG. A2. A user with glasses that create a significant leak might have a Tdm response of FIG. A3.

The problem arises when designing a system with significant ANR attenuation, for example, one in excess of 25 dB ANR performance in the 150 Hz region. When a suitable system is designed, one finds that the system suffers from oscillations when the headphone is not on the head, or being removed from the head. Often, the worst-case scenario is obtained when the unit is just being removed from the head and there is a significant leak. FIG. A4 is an example Tdm of a partially removed headphone, and FIG. A5 is a fully removed headphone. Although the oscillation of the system off the head is not generally harmful, it is annoying and is often deemed a defect by many users. The partially removed oscillation is potentially painful in systems capable of canceling high sound pressure levels, and is not acceptable or desirable to most users, or certainly undesirable.

The roots of the problem can be seen by comparing the Tdm of FIG. A2 with that of FIG. A4. The problem is there is over 180 degrees of phase shift. This puts a serious limitation on the loop gain that the system can have to not oscillate under any condition of partial removal. The limitation is that the gain be less than 1 before the phase shift is greater than 180 degrees.

If the open loop transfer function H1*H2*C*Tdm is designed to not oscillate partially off the head, then the type of Tdm shown in FIG. A2 from a tight fit, can cause potential low frequency oscillations because of the excessive gain in the very low frequencies, for example 10 Hz. At 10 Hz, the open loop gain will still be high, but the phase shift will be excessive.

A solution to this problem is to introduce one or more front-cavity vents. The vent is chosen to be equivelent to a small leak. This limits the variation in Tdm from user to user by establishing a leak or vent that is substantially independent or invariant to fit. FIG. A4 is an example of this. The Tdm is not affected significantly when the user has a leak created by fit because the vent leak is acoustically in parallel with the leak around the cushion.

As a result of an appropriate vent, the difference in response between any fit, and a partially removed fit has significantly less gain and phase difference, allowing for an open loop response with more gain with out partially removed or off head oscillations.

To avoid a significant impact on passive attenuation at higher frequencies, the vent is chosen to have a high acoustic impedance as the frequencies rise. A duct or tube, for example, has an equivelent impendance analogy of a parallel resistor and inductor.

The vent can also be made to be of a higher order. FIG. A6, in which the impedance rise can be greater than that of a simple vent with only a parallel resistive and inductive element. Higher order vents are possible. They are accomplished by creating a vent-cavity-vent . . . structure. A duct-cavity-duct structure creates a 4th order filter, where a simple duct creates a first or 2nd order filter, depending on if the impedance is domanantly resistive or inductive.

In designs with very good passive attenuation, higher order vents are generally desired. The affect on the Tdm of the system makes it desirable to design the vent such that its effect on the Tdm does not have adverse resonances. This leads to slightly more complex designs were the single duct might be replaced by two ducts of different dimensions, such as one dominated by inductance, and the other by resistance. The vents can also be a simple hole, or a hole with a resistive cloth or foam covering it.

FIG. A1 also shows a novel method of injecting the communication signal into the ANR system. The obvious way to do this is to inject the signal at the first summing point. This produces a response that is fairly flat, and can be described, at the sense microphone as:

$$G=Vo/Vcom=E1*E2*H1*H2*C*Tdm/(1-H1*H2*C*Tdm),$$

where
E1 is a fixed equalization
E3=1
E2 is a user settable tone control.

E1 is chosen to create the desired frequency response to communications signals. The injection of the signal into H2 allows for significant easing of the dynamic range issues. Since the open loop response of E1 and E2 are chosen to optimize ANR, there tends to always be a significant attenuation of high frequencies to maintain stability at high frequencies. If the signal is injected in the traditional manner, this causes E1 to have significant gain at high frequencies to over come this attenuation. Injecting the processed signal out of the Tone EQ into the appropriate component of the sallen-key filter produces a bypass of the high frequencies of most of the circuitry, avoiding the cumulative distortion of several stages of electronic amplifiers. This also eliminates significant gain in E1, and improves the signal-to-noise ratio or dynamic range or both significantly, contributing to high fideltity.

FIGS. B and C show several exemplary front-cavity venting schemes. FIG. B shows several possible venting methods that are applied to the front cavity. The figures show a separate resistive vent Rv, and duct vent Lv. In practice, this can be lumped into a duct type vent by choosing the dimensions so as to have the desired acoustic resistance and reactance.

Higher order vents can also be applied to back cavities with the desirable result of improved passive noise reduction over simple first and second order vents, and tuning the impedance seen by the driver.

It may also be desirable to couple a front cavity vent compliance (FIG. B4's C1 for example) to the back cavity compliance, creating a coupled vent. The back cavity is generally a large compliance and may be beneficial in damping a vent's acoustic response.

FIG. C shows the use of higher order vents on a vented pole piece driver. This has advantages in that the noise coming in the back cavity is coupled only to the pole piece vent, which is already a low pass filter. The resistive vents on the back of the driver that work at higher frequencies are not coupled directly to the outside noise pressure. This results in improved passive attenuation. The diaphragm of the driver, coupled to a voltage source through the driver motor, is a high impedance to the acoustic signals.

FIG. D1 shows a cross-sectional-type view of ANR earcup assembly with front-cavity vent X1 incorporated into the annular earseal backing X that engages in, for example, an interference fit, with earcup Y. Backing X mounts to earcushion Z via adhesive, velcro, screws, or other fasteners (not shown). Detail view A in FIG. D1 shows that the height of the vent or duct is much less than its width, giving it a dominant resistive as opposed to inductive characteristic. FIG. D2 shows another view of vent X1, particularly its location on a rounded corner portion of ear-seal backing X, labeled X' in the Figure.

FIG. E shows that a commercial ANR headset, such as those using so-called "Tri-port Technology" and available from Bose Corporation of Massachuset can also be modified to include to a front-cavity venting. The earcup shown includes an n-th order vent at the top portion. However, the vent or vents may be incorporated in accord with one or more of the embodiments in this disclosure and indeed with others not necessarily shown in explicit detail.

FIG. F1 shows a cross-section of one half of an automatic-noise-reduction (ANR) headset, specifically an exemplary earcup 100 in accord with the present invention. Earcup 100 includes an outer-cup assembly 110 and an inner-cup assembly (or active-circuitry module) 120. (For clarity, a second earcup, and connecting bridge member are not shown.) Outer-cup assembly 110 includes an outer cup 112, an annular ear cushion 114, an acoustic-damping layer 116, a vent opening 118.

In operation, outer-cup assembly 110 fits over an ear and against the head of a user, represented generally as surface 111, defining a substantially closed front air cavity (or volume) 119. The exemplary embodiment relies on a leak 115 between ear cushion 114 and surface 111 to provide a pressure release for front cavity 119. The pressure release allows driver (122.2) to move more freely at low frequencies where the "back cavity" volume becomes stiff. This greatly increases driver efficiency greatly improving battery life and headroom. In the exemplary embodiment, the leaks exist between the cushion of the earcup and the surface of a user's head. However, other embodiments vent the front cavity of the earcup through a tube or other type passage to the outside. For example, one embodiment places a tube through the ear cushion or provides an air passage in an interface structure which mounts the cushion to the outer cup. Other embodiments include one or more front-cavity vents in accord with one or more other portions of this disclosures.

The exemplary embodiment of inner-cup assembly 120 provides at least two advantages. First, it can tested prior to being installed in an earcup. And second, ti can be used to augment a passive headset with an ANR function. For example, a manufacturer or end-user of passive headsets can simply acquire and an inner-cup assembly as components and install them in the earcups of passive headsets, with very little modifications. It may also be feasible to replace an inner-cup assembly in a headset with an upgraded or advanced version of the inner-cup assembly.

In particular, inner-cup assembly 120 includes a front (ear-facing) portion 122, a back cavity 124, a back portion 126, and an outlet vent or tube 128. Front portion 122 includes a planar portion 122.1, an ANR driver 122.2, a driver shroud 122.3, an ANR sensor or microphone 122.4, and side walls 122.5.

Planar portion 122.1 extends generally to engage one or more portions of the interior surface of outer cup 112 and/or acoustic damping layer 116 to facilitate holding inner-cup assembly 120 fixed relative to outer cup assembly 110. Though not shown in the Figure, the exemplary embodiment glues the inner-cup assembly into the outer cup. However, in other embodiments, the interior surface of outer cup 65 includes one or more projections or holes which engage or mate in an interference fit with one or more corresponding holes or projections on planar portion 122.1 (or more generally inner-cup assembly 120). Some embodiments can provide extra holes or projections in the outer cup to allow for adjusting position of the inner-cup assembly within the outer cup and/or extra holes or projections on the inner-cup assembly for mating with different types of outer cups.

ANR driver (or acoustic transducer) 122.2, which defines a central driver axis 122.21, is supported within driver shroud 122.3. The present invention is not limited to any particular driver or class of drivers.

Shroud 122.3 includes a front annular flange 122.31 and a back annular flange 122.32. Front annular flange 122.31 extends forward from driver 122.2 toward surface 111 and defines a reduced driver aperture 122.33, centered on driver axis 122.21. In operation, the reduced driver aperture suppresses or mitigates cone-breakup in the driver and thus indirectly extends the cancellation bandwidth of the ANR circuitry and/or simplifies its filter requirements by suppressing or reducing the peaks of high-frequency resonances. Additionally, the inner-cup assembly itself damps the outer cup by providing a constrained layer between the inner and outer cup, improving attenuation of high frequencies.

In the exemplary embodiment, aperture 122.33 is circular; however, in other embodiments, flange 122.31 has multiple fingers that define the aperture as a star-like opening. Some embodiments may augment aperture 122.33 with holes distributed around the aperture. And still other embodiments may replace aperture 122.33 with a set of holes concentrated around the driver axis or distributed uniformly across a dome or other structure covering the driver. In general, it is believed that any driver-shroud structure that presents a reduced view of driver 122.2 lies within the scope of the invention.

In addition to front annular flange 122.31, driver shroud 122.3 includes back annular flange 122.32. Back annular flange 122.32 projects perpendicularly from planar portion 122.1 of front portion 122, surrounding and engaging ANR driver 122.2.

In other embodiments, the back annular flange consists of a set of two or more annular flange segments or spaced fingers that impinge on and thus secure the driver in place. However, some embodiments glue, screw, or otherwise secure the driver to front portion 122. Still other embodiments may form a driver having an integral or non-integral structure for providing a reduce aperture and/or serving the function of planar portion 122.1. Thus, the present invention is not limited to any particular frontal structure.

In addition to planar portion 122.1, ANR driver 122.2, and driver shroud 122.3, front portion 122 also includes an ANR sensor or microphone 122.4.

ANR sensor 122.4, for example, an electret microphone, is mounted in or on planar portion 122.1 a distance $X_{DM}$ from central driver axis 122.21. Distance $X_{DM}$ is chosen using known principles for making and using ANR headsets.

Sidewall 122.5 which extends back from planar portion 122.1 to engage back portion 126, thereby defining back cavity 124. More specifically in the exemplary embodiment, sidewall 122.5 extends back from planar portion 122.1 toward central driver axis 122.21 to define a surface in general conformity with adjacent portions of outer cup 112. Sidewall 122.5 terminates with an annular shelf or rim 122.51 that engages a peripheral or perimeter face 126.1 of back portion 126.

As shown in the figure, the exemplary embodiment provides an upper portion 122.51 of sidewall 122.5 with a different contour than that of its lower portion 122.52.

However, other embodiments can provide a sidewall with a uniform contour. Additionally, other embodiments may omit all or one or more portions of the sidewall from front portion 122 and add a complete sidewall or one or more sidewall portions to back portion. For example, some embodiments may provide the front and back portions each with complete peripheral sidewalls that engage each other to define the back cavity, in roughly the fashion of two hemispheres engaged to form a sphere. Or, some embodiments may provide the front and back portions with sidewall segments that mate in an interleaved or "interdigitated" manner to define the back cavity. Additionally, some embodiments define the back cavity by sizing planar portion 122.1 to effectively partition the interior volume of earcup into acoustically separate volumes, thereby obviating engagement of the front portion with the back portion. This can be done by extending the planar portion to contact the acoustic damping layer. (In some variants of this embodiment, the planar portion would include a channel covered by another planar member to form an air passage that mates with vent opening 118. This air passage could be tapered and/or filled with foam or other to restrict air flow.) In general, it is believed that the invention is not limited to any particular structure for defining the back cavity.

Back portion 126 includes a circuit board 126.2. Circuit board 126.2 includes a connector 126.21 and circuitry 126.22. Although the exemplary embodiment includes circuitry 126.22 in the form of ANR circuitry, other embodiments may also provide a variety of other circuits, such as wireline or wireless communication circuits.

Outlet vent or tube 128 extends from vent opening 118 in outer cup through an opening 122.53 in sidewall 122.5 of front portion 122. In this exemplary embodiment, the vent comprises a tube 128.1 with a restrictive opening 128.2. The restrictive opening provides a significant resistive component which, if made sufficiently large, prevents the inductance of the tube from resonating with the back cavity. Such resonance will add significant impedance to the back of the driver and cause system response to dip. Tube resistance can be increased, for example, by tapering the tube and/or inserting screen, foam, or other flow restriction into it. The vent tube provides a pressure release from the back of the driver without venting to the inside cup. For aviation applications, this release allows for ambient pressure changes experienced when a plane changes altitudes.

FIG. F2 shows a simplified equivalent electric circuit 200 for the acoustics of exemplary earcup 110 in FIG. 1. Circuit 200 includes:
capacitor $C_D$ which represents ANR driver compliance;
inductor $M_D$ which represents mass of the ANR driver;
resistor $R_D$ which represents damping of the ANR driver;
resistor $R_E$ which represents voice coil resistance of the ANR driver;
transformer ratio 1:BL which represents force factor of the driver;
capacitor $C_B$ represents compliance of the back cavity;
inductor $L_V$ represents the vent
resistor $R_V$ represents the vent
$C_F$ is the compliance of the front cavity
$L_L$ is the inductance of leaks around the seal
$R_L$ is the resistance of leaks around the seal.

This simplified equivalent circuit provides the following insights regarding size and placement of vent 128. If resistor $R_V$, the restriction of vent 128 from the inner-cup assembly, is small, then at the resonance frequency of $L_V$ and $C_B$, which respectively represent the vent inductance and back-cavity compliance, the impedance will become infinite. Thus, it is desirable to make resistor $R_V$ sufficiently large to provide a damping effect. On the other hand, if the vent is closed, the driver must overcome the stiffness of the back cavity, causing a significant loss in efficiency. And, if the vent outlets to the front cavity, rather than outside the earcup, it will act, at low frequencies, as a short across capacitors $C_B$ and $C_F$, greatly reducing the output efficiency of the driver.

FIG. F3 is an exploded view of an exemplary active-noise-reduction headset 300 incorporating teachings of the present invention. One or more front-cavity vents, in accord with one or more other portions of this disclosure are also included.

FIG. F4 includes front, side, and back views of a bottom housing shown in FIG. F3.

FIG. F5 includes front, side, and back views of a top housing shown in FIG. 3.

CONCLUSION

The embodiments described above are intended only to illustrate and teach one or more ways of practicing or implementing the present invention, not to restrict its breadth or scope. The actual scope of the invention, which encompasses all ways of practicing or implementing the concepts of the invention, is defined by the following claims and their equivalents.

I claim:

1. An active-noise-reduction (ANR) system for a user having a head, an ear, and mouth, the system comprising:
an ear cup for placement over the ear and against the head of the user, with the earcup having an ANR driver positioned between a back cavity in the earcup and a front cavity in the earcup, the front cavity adjacent the ear of the user when the earcup is placed over the ear;
an ANR microphone positioned within the earcup;
ANR closed-loop control circuitry coupled to the ANR driver and the ANR microphone;
a boom microphone coupled to the ANR closed-loop control circuitry; and
means for limiting effect of user fit variations on stability of the ANR closed-loop control circuitry, with the means including a substantially user-invariant air passage in fluid communications with the front cavity and an exterior of the earcup.

2. The active-noise-reduction system of claim 1, wherein the air passage comprises a tube having one open end coupled to the front cavity and an another open end coupled to the exterior.

3. The active-noise-reduction system of claim 1, wherein the substantially user-invariant air passage has an n-th order acoustic characteristic, with n being two or more.

4. The active-noise-reduction system of claim 1, wherein the air passage is in parallel with leakage between the front cavity and the exterior of the earcup when the earcup is engaged against the head of the user.

5. The active-noise-reduction system of claim 1,
wherein the earcup comprises a dome, a cushion, and an ear-seal member positioned between a front edge face of the dome and the cushion, wherein the ear-seal member defines at least a first portion of the air passage.

6. The active-noise-reduction system of claim 5, wherein the cushion includes a second portion of the air passage which is in fluid communication with the first portion.

7. The active-noise-reduction system of claim 1, wherein the air passage has an equivalent electrical circuit comprising an inductance in parallel with a resistor.

8. The active-noise-reduction system of claim 1, wherein the air passage has an acoustic impedance that increases with increasing frequency.

9. The active-noise-reduction system of claim 1,
wherein the ANR driver includes a diaphragm and an annular pole piece, with the annular pole piece defining an central air passage to a rear portion of the diaphragm; and
wherein the back cavity includes an annular cavity defining an air passage through the back cavity, with the air passage through the back cavity aligned with the central air passage in the annular pole piece to allow fluid communication between the rear portion of the diaphragm and an exterior of the earcup.

10. The active-noise-reduction system of claim 1, wherein the ANR closed-loop control circuitry has a frequency response characteristic defined as a ratio of an electrical input to the ANR driver to an electrical output of the ANR microphone, and wherein the means for limiting effect of user fit variations on stability of the ANR control circuitry limits effect of user fit variations on the ratio.

11. The active-noise-reduction system of claim 1, wherein the ANR circuitry provides in excess of 25 dB of cancellation in a frequency region around 150 Hertz.

* * * * *